US010501548B2

(12) United States Patent
Soldo et al.

(10) Patent No.: US 10,501,548 B2
(45) Date of Patent: Dec. 10, 2019

(54) METHODS FOR DETECTING 1,25-DIHYDROXYVITAMIN D AND RELATED ANTIBODIES

(71) Applicant: Diasorin S.p.A., Saluggia, Vercelli (IT)

(72) Inventors: Joshua Soldo, Prior Lake, MN (US); Gregory Olson, Lakeland, MN (US); Michael Lutterman, New Brighton, MN (US); John Wall, Woodbury, MN (US); Michael New, Bloomington, MN (US); Hector Floyd Deluca, Deerfield, WI (US); Fabrizio Bonelli, Alessandria (IT)

(73) Assignee: DiaSorin S.p.A., Saluggia (IT)

( * ) Notice: Subject to any disclaimer, the term of this patent is extended or adjusted under 35 U.S.C. 154(b) by 148 days.

(21) Appl. No.: 15/606,284

(22) Filed: May 26, 2017

(65) Prior Publication Data
US 2017/0267770 A1 Sep. 21, 2017

Related U.S. Application Data

(62) Division of application No. 14/763,264, filed as application No. PCT/EP2014/051482 on Jan. 27, 2014, now Pat. No. 10,196,449.

(30) Foreign Application Priority Data

Jan. 28, 2013 (EP) ..................................... 13152851

(51) Int. Cl.
G01N 33/82 (2006.01)
C07K 16/28 (2006.01)
C07K 16/26 (2006.01)

(52) U.S. Cl.
CPC .......... *C07K 16/2869* (2013.01); *C07K 16/26* (2013.01); *G01N 33/82* (2013.01); *C07K 2317/32* (2013.01)

(58) Field of Classification Search
CPC C07K 16/26; C07K 16/2869; C07K 2317/32; G01N 33/82
See application file for complete search history.

(56) References Cited

U.S. PATENT DOCUMENTS

| 4,816,417 | A | 3/1989 | DeLuca et al. | |
| 4,840,895 | A * | 6/1989 | Self | C07K 16/42 435/18 |
| 6,516,294 | B1 | 2/2003 | Norman | |
| 10,196,449 | B2 | 2/2019 | Soldo et al. | |
| 2012/0064533 | A1 * | 3/2012 | Lawlor | C07K 16/18 435/6.12 |
| 2012/0094396 | A1 | 4/2012 | Petkovich et al. | |
| 2015/0361178 | A1 | 12/2015 | Soldo et al. | |
| 2017/0267770 | A1 | 9/2017 | Soldo et al. | |
| 2017/0322230 | A1 * | 11/2017 | Colotta | G01N 33/82 |

FOREIGN PATENT DOCUMENTS

| EP | 0177531 | | 1/1991 |
| EP | 0583945 | | 2/1994 |
| EP | 2759550 | | 7/2014 |
| EP | 2759551 | | 7/2014 |
| WO | WO 1989/001631 | | 2/1989 |
| WO | WO 2008/092917 | | 8/2008 |
| WO | WO 2012/066003 | * | 5/2012 |
| WO | WO 2013/043310 | | 3/2013 |
| WO | WO 2014/114780 | | 7/2014 |

OTHER PUBLICATIONS

Singarapu et al., "Ligand-Specific Structural Changes in the Vitamin D Receptor in Solution," Biochemistry, 2011, vol. 50, No. 51, pp. 11025-11033.*
Smit et al., "Comparison of four different assays for determination of serum S-100B," Int. J. Biol. Markers, 2005, vol. 20, No. 1, pp. 34-42.*
Anderson, J.L., et al. (2011) "*Parathyroid Hormone, Vitamin D, Renal Dysfunction, and Cardiovascular Disease: Dependent or Independent Risk Factors?*," Am. Heart J. 162(2):331-339.
Arai, M.A. et al. (2007) "High-Throughput System For Analyzing Ligand-Induced Cofactor Recruitment By Vitamin D Receptor," Bioconjug. Chem. 18(3):614-20.
Arnaud, J. et al. (1993) "*Affinity Differences For Vitamin D Metabolites Associated With The Genetic Isoforms Of The Human Serum Carrier Protein (DBP)*," Hum. Genet. 92(2):183-188.
Chesney, R.W., et al. (1981) "*The Circulating Parathyroid Hormone (PTH) to Calcitriol ($1,250H_2D$) Ratio: A Means of Evaluating Calcitriol Synthesis in Disorders of Calcium Metabolism*," Pediatric Res. 15(Suppl4):505.
Costagliola, S. et al. (1998) "*Genetic Immunization Against the Human Thyrotropin Receptor Causes Thyroiditis and Allows Production of Monoclonal Antibodies Recognizing the Native Receptor*," J. Immunol. 160(3):1458-1465.
European Extended Search Report EP 13152851.5 (dated 2013) (7 pages).
Harlow, E. (1988) "*Antibodies, A Laboratory Manual*," Cold Spring Harbor Laboratory Press, Cold Spring harbor, NY; pp. 1-99.

(Continued)

*Primary Examiner* — Galina M. Yakovleva
(74) *Attorney, Agent, or Firm* — Jeffrey I. Auerbach; AuerbachSchrot LLC

(57) ABSTRACT

There is disclosed an assay method for selectively detecting 1,25-dihydroxy-vitamin D in a biological fluid sample. According to the method, the pH of the test sample is adjusted to 6-9 and a receptor protein comprising the Ligand Binding Domain of Vitamin D Receptor (VDR-LBD) is added to the test sample, thereby obtaining the formation of a VDR-LBD/1,25-dihydroxyvitamin D complex in which the VDR-LBD portion is conformationally changed with respect to unbound VDR-LBD. The VDR-LBD/1,25-dihydroxyvitamin D complex is then detected by means of a capture moiety which is capable of specifically binding to VDR-LBD bound to 1,25-dihydroxyvitamin D. Also disclosed are an assay kit and an antibody for carrying out the method. The assay is preferably a sandwich immunoassay.

7 Claims, 8 Drawing Sheets
Specification includes a Sequence Listing.

(56) References Cited

OTHER PUBLICATIONS

Haussler, M.R. et al. (1998) "*The Nuclear Vitamin D Receptor: Biological and Molecular Regulatory Properties Revealed*," J. Bone Mineral Research 13(3):325-349.
Holick, M.F. et al. (2007) "*Vitamin D Deficiency*," NEJM 357:266-281.
Holick, M.F. et al. (2008) "*Vitamin D Deficiency: A Worldwide Problem With Health Consequences*," Amer. J. Clin. Nutrit. 87(suppl):1080S-1086S.
International Search Report PCT/EP2014/051482 (WO 2014/114780) (dated 2014) (5 pages).
International Search Report PCT/IB2016/050230 (WO 2016/113720) (dated 2016) (4 pages).
Jones, G. et al. (1998) "*Current Understanding of the Molecular Actions of Vitamin D*," Physiological Reviews 78(4):1193-1231.
Lucas, P.A., et al. (1983) "*Ratio of Parathyroid Hormone to 1,25-dihydroxycholecakiferol in Early Renal Failure*," Kidney Int. Suppl. 16:S171-S174.
Mangelsdorf, D.J. et al. (1995) "*The Nuclear Receptor Superfamily: The Second Decade*," Cell 83(6):835-839.
Notice of Opposition Filed Regarding EP 13152851.5 (2018) (19 pages).
P11473 (VDR_Human) (2016) UniProtKB/Swiss-Prot Printout (11 pages).
Patel, S., et al. (2011) "*Changes in Bone Mineral Parameters, Vitamin D Metabolites, and PTH Measurements with Varying Chronic Kidney Disease Stages*," J. Bone Miner. Metab. 29:71-79.
Printout retrieved from https://en.wikipedia.org/wiki/Antigen-antibody_interaction on Dec. 1, 2017 (2 pages).
Rachez, C. et al. (1999) "*Ligand-Dependent Transcription Activation By Nuclear Receptors Requires The DRIP Complex*," Nature 398(6730):824-828.
Response to Third Party Observations Filed Regarding EP 13152851.5 (2017) (5 pages).
Rochel, N., et al. (2000) "*The Crystal Structure of the Nuclear Receptor for Vitamin D Bound to Its Natural Ligand*," Mol. Cell 5:173-179.
Rudikoff, S., et al. (1982) "*Single Amino Acid Substitution Altering Antigen-Binding Specificity*," Proc. Natl. Acad. Sci. USA 79:1979-1983.
Scheefers-Borchel, U. et al. (1985) "*Discrimination Between Fibrin And Fibrinogen By A Monoclonal Antibody Against A Synthetic Peptide*," Proc. Natl. Acad. Sci. (U.S.A.) 82:7091-7095.
Self, C.H. et al. (2013) "*Non-Competitive Immunoassays For Small Molecules—The Anti-Complex And Selective Antibody Systems*," In: The Immunoassay Handbook, pp. 61-65.
Staal, A. et al. (1996) "*Distinct Conformations Of Vitamin D Receptor/Retinoid X Receptor-Alpha Heterodimers Are Specified by Dinucleotide Differences In The Vitamin D-Responsive Elements Of The Osteocalcin And Osteopontin Genes*," Molec. Endocrinol. 10(11):1444-1456.
Swami, S., et al. (2001) "*A New Enzyme-Linked Immunosorbant Assay for the Measurement of Human Vitamin D Receptor*," Bone 28(3):319-326.
Third Party Observations Filed Regarding EP 13152851.5 (2017) (6 pages).
Väisänen, S., et al. (1997) "*Conformational Studies of Human Vitamin-D Receptor by Antipeptide Antibodies, Partial Proteolytic Digestion and Ligand Binding*," Eur. J. Biochem. 248:156-162.
Wang, Y., et al. (2012) "*Where is the Vitamin D Receptor?*," Arch. Biochem. Biophys. 523:123-133.
Written Opinion of the International Searching Authority PCT/EP2014/051482 (WO 2014/114780) (dated 2014) (6 pages).
Written Opinion of the International Searching Authority PCT/IB2016/050230 (WO 2016/113720) (dated 2016) (6 pages).
Yang, W. et al. (1999) "*20-Epi Analogues Of 1,25-Dihydroxyvitamin D3 Are Highly Potent Inducers Of DRIP Coactivator Complex Binding To The Vitamin D3 Receptor*," J. Biol. Chem. 274(24):16838-16845.

\* cited by examiner

METHODS FOR DETECTING 1,25-DIHYDROXYVITAMIN D AND RELATED ANTIBODIES

CROSS-REFERENCE TO RELATED APPLICATIONS

This is a divisional application of U.S. Ser. No. 14/763,264 filed Jul. 24, 2015, which claims priority to the national stage application filed under 35 U.S.C. § 371 of international application PCT/EP2014/051482, filed under the authority of the Patent Cooperation Treaty on Jan. 27, 2014, published; which claims the benefit of Patent Application No. EP 13152851.5 filed on Jan. 28, 2013. The entire disclosures of all the aforementioned applications are expressly incorporated herein by reference for all purposes.

SEQUENCE LISTING

The instant application contains a Sequence Listing which has been submitted via EFS-web and is hereby incorporated by reference in its entirety. The ASCII copy, created on Jul. 13, 2015, is named 3934_59290_SEQ_LIST_E0098708-Div.txt, and is 3.89 KB in size.

BACKGROUND OF THE INVENTION

The present invention relates to a method and kit for detecting total 1,25-dihydroxy-vitamin D in a biological fluid sample, such as whole blood, plasma, serum, or urine sample.

More in particular, the present invention relates to an immunoassay method and kit, as well as to the related antibodies, suitable for detecting total 1,25-dihydroxyvitamin D in a biological fluid sample which may contain 1,25-dihydroxyvitamin D together with other non active forms of vitamin D, such as 25-hydroxyvitamin D.

Vitamin D is a steroid hormone which plays a fundamental role in skeletal metabolism and calcium homeostasis. In humans and animals, the major forms of vitamin D are vitamin $D_3$ (cholecalciferol) and vitamin $D_2$ (ergocalciferol). Vitamin $D_3$ is primarily synthesized in the skin from 7-dehydrocholesterol in response to exposure to solar ultraviolet-B (UVB), but vitamin intake can also occur from dietary sources such as oily fish, i.e. salmon and mackerel. Vitamin $D_2$ is primarily acquired in the diet from fungal and vegetable sources as well as from supplementation (e.g. Drisdol™ or Sterogyl 15 "A").

Irrespective of the source, the conversion of vitamins $D_2$ and $D_3$ into a bioactive compound requires two separate hydroxylation steps. In the liver, the enzyme 25-hydroxylase converts vitamin D to 25-hydroxyvitamin D (hereinafter designated as "25(OH)D"). This intermediary metabolite is the major circulating form of the hormone and serves as a reservoir for further hydroxylation to the biologically active metabolite 1,25-dihydroxyvitamin D (hereinafter designated as "1,25(OH)$_2$D").

The latter step takes place primarily in the renal tubular cells and is catalyzed by the enzyme 1-alpha-hydroxylase. The plasma concentrations of 1,25(OH)$_2$D are highly regulated by a variety of factors, including the serum parathyroid hormone (PTH), and they are normally about 1000-fold lower than the precursor compound 25(OH)D.

Because of their lipophilic nature, the majority of vitamin D and metabolites thereof circulate in the blood-stream bound to the vitamin D binding protein (DBP) (80-90%), also known as Gc-Globulin, and albumin (10-20%). DBP has high affinity for vitamin D metabolites ($Ka=5\times10^8 M^{-1}$ for 25(OH)D and 24,25(OH)$_2$D, $4\times10^7 M^{-1}$ for 1,25(OH)$_2$D and vitamin D), such that under normal circumstances only approximately 0.03% 25(OH)D and 24,25(OH)$_2$D and approximately 0.4% 1,25(OH)$_2$D are in a free form.

The biological effects of 1,25(OH)$_2$D are mediated primarily by the binding of this bioactive hormone to a specific intracellular Vitamin D Receptor (VDR), which acts primarily by regulating the expression of genes whose promoters contain specific DNA sequences known as Vitamin D Response Elements (VDREs).

The Vitamin D Receptor (VDR) is a ligand-dependent transcriptional regulator belonging to the superfamily of nuclear receptors (NRs). Like the other members of this receptor family, the VDR possesses a modular structure which comprises an amino-terminal A/B domain, a highly conserved DNA-Binding Domain (DBD), a flexible linker region and a C-terminal Ligand-Binding Domain (LBD) which is more variable (Mangelsdorf D J et al., 1995, *Cell* 83(6):835-9). The C-terminal LBD is a globular multifunctional domain, responsible for hormone binding, dimerization with Retinoid X Receptor (RXR) and interaction with co-repressors and co-activators, which all together are critical for the regulation of transcriptional activities (Haussler M R, et al. 1998, *J Bone Miner Res.* 13(3):325-49).

The Ligand Binding Domain (LBD) of VDR has been crystallized and its structure solved (Rochel N, Wurtz J M, Mitschler A, Klaholz B, Moras D The crystal structure of the nuclear receptor for vitamin D bound to its natural ligand. Mol Cell 2000; 5:173-179).

The binding of the ligand to the VDR induces a conformational change at the Ligand Binding Domain of the receptor, which in turn increases heterodimerization of VDR with a cofactor, the Retinoid X Receptor (RXR), on a Vitamin D-Responsive Element (VDRE) in the promoter region of the target genes. This in turn leads to opening of the promoter to the transcriptional machinery (Glenville J. et al., 1998 *Physiological Reviews* 78(4):1193-1231).

Nuclear receptor Ligand Binding Domains (LBDs) are known to have a high content of alpha-helix, which may undergo a large conformational change in response to ligand binding, forming up a hydrophobic pocket. Recently, differences in the conformation of the *Rattus norvegicus* Ligand-Binding Domain (r-VDR-LBD) when bound to diverse ligands were solved by NMR spectroscopy (Kiran K. Singarapu et al. 2011 *Biochemistry* 50 (51): 11015-24).

Vitamin D is currently recognized as a pro-hormone which has multiple roles in maintaining optimal health in human beings. It has long been established that marked vitamin D deficiency results in histologically evident bone diseases such as osteomalacia in adults and rickets in children, while vitamin D insufficiency may cause alterations in the parathyroid hormone concentration which, if persisting over time, may contribute to bone loss and fracture. However, although initially identified as a classic regulator of calcium homeostasis, vitamin D is now known to have a broader spectrum of actions, driven by the wide expression and distribution in human tissues of the vitamin D receptor (VDR).

In the last decades, clinical and epidemiological data have provided several evidences that impaired levels of 25(OH)D are associated with an increasing risk of various chronic diseases including cardiovascular diseases, hypertension, myocardial infarction, diabetes, cancer, reduced neuromuscular function, infectious and autoimmune diseases. Even complications of pregnancy such as pre-eclampsia, gestational diabetes, cesarean section, and premature birth might be the tragic sequela of gestational vitamin D deficiencies (Holick M F; 2007 *N Engl J Med.* 357(3):266-81, Holick M F and Chen T C. 2008 *Am J Clin Nutr.*; 87(4): 1080S-6S).

However, very few studies have been carried out to associate risks of chronic disease to 1,25(OH)$_2$D levels, due to both complexity and lack of reliability of the measurement methods which are available today.

Therefore, the determination of circulating 1,25(OH)$_2$D, which is the active form of vitamin D, is becoming of increasing relevance in many different clinical applications, either as a diagnostic marker and/or as a therapy monitoring indicator. For instance, the determination of serum 1,25 (OH)$_2$ D and parathyroid hormone (PTH) levels and a possible correlation thereof may represent an important measure for aiding in the diagnosis of parathyroid diseases as well as for the detection of the onset of secondary hyperparathyroidism in the course of renal failure or the development of vitamin D-resistant rickets (VDRR).

Currently, both in routine clinical and research use there is a wide range of methodologies available for measuring the circulating levels of total 25(OH)D (i.e., 25(OH)D$_3$+25(OH) D$_2$). Commercial, fast, automated chemiluminescence-based immunoassay methods are supplied by Abbott Diagnostics (Abbott Park, Ill., USA, ARCHITECT 25-OH vitamin D assay), DiaSorin Inc. (Stillwater, Minn., USA, LIAISON® 25 OH Vitamin D Total Assay), Immunodiagnostic Systems (Boldon, England, IDS-iSYS 25-Hydroxy Vitamin D (25OHD)), Roche Diagnostics (Mannheim, Germany, Modular Analytics E170 Elecsys® Vitamin D Total assay), and Siemens Healthcare Diagnostics (Tarrytown, N.Y., USA, ADVIA Centaur® Vitamin D Total assay). Besides these assay platforms, there has recently been a steady increase in the use of physical methods based on chromatographic separation followed by non-immunological direct detection (semi-automated liquid chromatography-tandem mass spectrometry, LC-MS/MS), which have been principally developed in specialist laboratories in the United States (e.g. Esoterix Inc. in Calabasas Hills, Calif., Mayo Clinic in Rochester, Minn., ARUP Laboratories in Salt Lake City, Utah and Quest Diagnostics in Lyndhurst, N.J.), Europe (e.g. Ghent University in Ghent, Belgium, and CHU de Liege in Liege, Belgium) and Australia (e.g. Pathology Queensland in Herston Queensland, and Douglass Hanly Moir Pathology in Macquarie Park NSW).

Despite the wide selection of assay platforms for measuring 25(OH)D, there are no automated assay methods currently available for the quantitative determination of the active form of vitamin D in clinical samples. The systemic circulating levels of 1,25(OH)$_2$D are extremely low, in the pg/ml range, and therefore represent a significant bioanalytical challenge for clinical monitoring. Quantitation of 1,25(OH)$_2$D in plasma has been traditionally carried-out by radioimmunoassay (RIA). In order to avoid problems related to handling of radioactivity and the limited shelf-life of radioactive labels, new vitamin D testing methods have recently emerged which mainly rely upon the employment of the LC-MS/MS methodology. However, the reported LC-MS/MS bioanalytical assays for 1,25(OH)$_2$D suffer from the extensive sample preparation procedures or derivatization protocols which need to be carried out in order to achieve the requisite sensitivity and selectivity. At present, the main methods available for the detection of 1,25(OH)$_2$D require performing a number of sample pre-treatment or pre-analytical steps which are usually carried-out manually and may therefore be very time consuming, labor intensive, and expensive.

EP 0 583 945 A discloses an assay for 1,25(OH)$_2$D which involves extracting blood serum using an organic solvent such as ethyl acetate, separating out potentially interfering other vitamin D metabolites using a silica column, and then adding pig receptor protein, radiolabeled 1,25(OH)$_2$D, biotinylated antibody capable of binding to the receptor, and a facilitator protein such as BSA as part of an immunoprecipitation competitive binding assay.

WO/8901631 discloses a competitive binding assay for 1,25(OH)$_2$D (3) which involves adding pig receptor protein, radiolabeled 1,25(OH)$_2$D and biotinylated antibody capable of binding to the receptor to untreated blood serum. The competitive binding assay requires the use of vitamin D transport protein which acts as a screen to minimize interference from related metabolites.

S. SWAMI et al., Bone, Vol. 28, No. 3, March 2001:319-326 discloses an antibody which binds to the hinge portion of the vitamin D receptor (VDR) and which is used in a method for the measurement of VDR. However, such antibody is not able to distinguish between ligand-occupied and -unoccupied VDR and is therefore not useful for the detection of 1,25(OH)$_2$D.

The DiaSorin RIA (Part No. 65100E/100 Tubes; 1,25-Dihydroxyvitamin D) involves the use of organic solvents, extraction instrumentation, and C18-OH columns to separate out potentially interfering vitamin D metabolites such as 24,25(OH)$_2$D, 25,26(OH)$_2$D and 25(OH)D in order to isolate 1,25(OH)$_2$D from the test sample prior to metabolite measurement.

Even the recently commercialized automated assay supplied by Immunodiagnostics for the determination of 1,25 (OH)$_2$D (Part No. IS-2400; IDS-iSYS 1,25-Dihydroxyvitamin D) requires a time-consuming and labor intensive sample pre-treatment step which makes use of the IDS proprietary Immunocapsules.

Furthermore, the prior art methods often suffer from limitations in term of assay specificity since cross-reactivity events with other vitamin D metabolites not completely removed from the test specimens during the pre-analytical or sample pre-treatment steps may lead to the measurement of erroneous higher concentrations of 1,25(OH)$_2$D. For example, most immunoassay antibodies significantly cross-react with 25(OH)D, 24,25(OH)$_2$D, and 25,26(OH)$_2$D which may be present in blood at levels 1000-fold greater than 1,25(OH)$_2$D.

There is therefore a strong need to develop an assay method for detecting total 1,25(OH)$_2$D (1,25(OH)$_2$D$_2$+1,25 (OH)$_2$D$_3$) which does not suffer from the drawbacks and limitations of the prior art.

In particular, there is a need for an assay method which would enable precise, sensitive and accurate detection of total 1,25(OH)$_2$D (1,25(OH)$_2$D$_2$+1,25(OH)$_2$D$_3$) without requiring time-consuming and labor intensive sample pre-treatment steps and which may possibly be provided in an automated format.

There is also a need for a 1,25(OH)$_2$D assay method which substantially does not cross-react with other vitamin D metabolites which may be present in the test sample.

These and other needs are met by the method, and the related kit and antibodies, as defined in the appended claims, which form an integral part of the description.

DETAILED DESCRIPTION OF THE PREFERRED EMBODIMENT(S)

Figure 1:
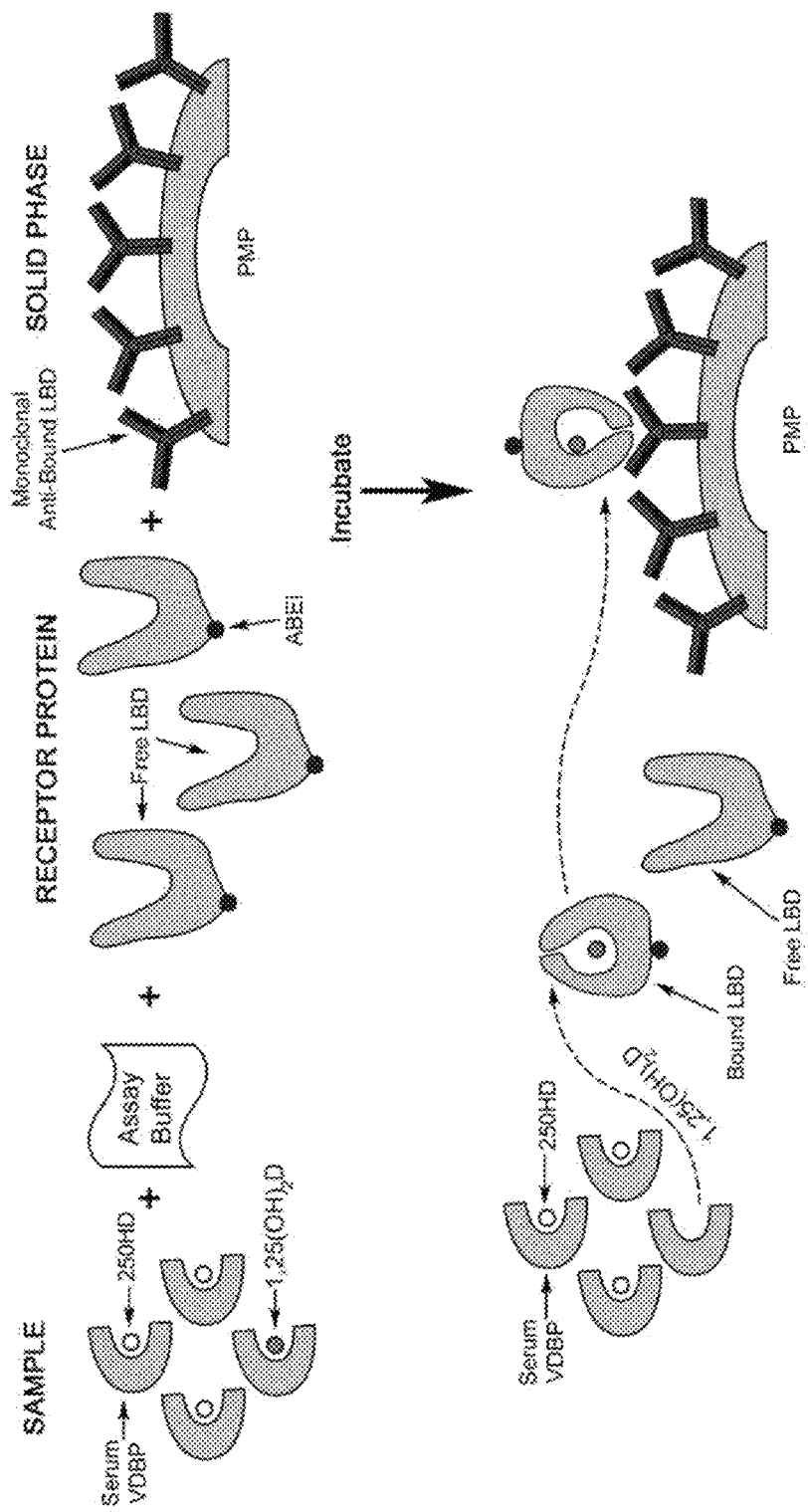
FIG. 1 and FIG. 2 illustrate one-site, non-competitive immunoassays, where the complex formed via the binding of 1,25(OH)$_2$D to the labeled receptor protein which comprises the Ligand Binding Domain of Vitamin D Receptor (VDR-LBD) that is captured by the conformation-specific capture antibody of the invention (which in FIG. 1 and FIG. 2 is designated as "Monoclonal Anti-Bound LBD") immobilized on a solid support.

As further illustrated in the examples below, the present invention is based on the finding that the pH of the medium in which the assay is performed significantly influence the binding affinity of vitamin D binding protein (DBP) and of the Ligand Binding Domain of Vitamin D Receptor (VDR-LBD) to $1,25(OH)_2D$.

More specifically, the results of experiments conducted by the present inventors clearly showed that a shift in the pH value of the test sample above 6, preferably above 7, surprisingly induces an increase of about 200-fold in the affinity of VDR-LBD for $1,25(OH)_2D$ over 25(OH)D, while at the same pH value DBP exhibits about 1000 fold greater affinity for 25(OH)D over $1,25(OH)_2D$. The exploitation of such an advantageous effect of the pH on the equilibrium between $1,25(OH)_2D$ bound to DBP and $1,25(OH)_2D$ bound to VDR-LBD represents therefore a unique tool in terms of both ease and effectiveness for selectively capturing circulating $1,25(OH)_2D$ from natural DBP in the presence of a molar excess of VDR-LBD, while leaving at the same time the majority of 25(OH)D in a sequestered form bound to DBP. Such an approach is particularly advantageous over the prior art methods, which require time-consuming and labor intensive sample pre-treatment steps to allow the determination of $1,25(OH)_2D$ in clinical samples.

Since the binding of $1,25(OH)_2D$ to VDR-LBD is known to induce a conformational change in the VDR-LBD molecule, the present inventors have conducted extensive experimentation to develop a capture moiety, such as an antibody, capable of specifically recognizing and binding to VDR-LBD bound to $1,25(OH)_2D$ without cross-reacting with uncomplexed VDR-LBD, in order to selectively discriminate the VDR-LBD/$1,25(OH)_2D$ complex from unbound VDR-LBD in various biological matrices. Such conformation-specific capture moiety is particularly useful, since it represents an invaluable tool for the rapid and reliable detection of the circulating active form of vitamin D.

Thus, one aspect of the present invention is a method for detecting $1,25(OH)_2D$ or analog thereof in a biological fluid sample, as defined in appended claim 9.

Also within the scope of the invention is a kit for detecting $1,25(OH)_2D$ or an analog thereof in a biological fluid sample.

The term "vitamin D" as used in the present description refers both to vitamin $D_3$ (cholecalciferol) and vitamin $D_2$ (ergocalciferol), and the term "$1,25(OH)_2D$" refers to both $1,25(OH)D_3$ and $1,25(OH)D_2$. Analogues of $1,25(OH)_2D$ include modified versions and structural analogues thereof, such as for example 19-nor-1α-25-dihydroxyvitamin $D_2$ (e.g. Zemplar or paricalcitol from Abbott), 1α-hydroxyvitamin $D_2$ or 1α-hydroxyergocalciferol (e.g. Hectorol or doxercalciferol from Genzyme), and 2-methylene-19-nor-(20S)-1α,25-$(OH)_2D_3$ (e.g. 2MD from Deltanoid Pharmaceuticals).

As mentioned above, a characterizing feature of the detection method of the present invention is that the pH of the biological fluid sample under examination is adjusted to a value above 6, i.e. comprised between 6 and 9. Preferred pH values are comprised between 7 and 8.6, such as 7.2, 7.3, 7.4, 7.5, 7.6, 7.7, 7.8, 7.9, 8.0, 8.1, 8.2, 8.3, 8.4, 8.5 or 8.6. Buffering agents and buffer solutions suitable for adjusting the pH of a biological fluid sample to the above mentioned values are well known to those skilled in the art.

In the context of the present invention, the biological fluid sample is preferably selected from the group consisting of whole blood, serum, plasma, and urine. The biological fluid sample may optionally include further components, such as for example: diluents, preservatives, stabilizing agents and/or buffers. If needed, dilutions of the biological fluid sample are prepared using any suitable diluent buffer known in the art.

The detection method of the present invention is further characterized in that a receptor protein comprising the Ligand Binding Domain of Vitamin D Receptor (VDR-LBD) is employed in order to bind $1,25(OH)_2$ D or analog thereof.

The term "receptor protein comprising the Ligand Binding Domain of Vitamin D Receptor (VDR-LBD)" as used in the present description encompasses both the whole Vitamin D Receptor protein (VDR), which includes the C-terminal Ligand Binding Domain, and the Ligand Binding Domain (LBD) of Vitamin D Receptor in an isolated or engineered form.

For example, the whole Vitamin D Receptor protein or the Ligand Binding Domain thereof is a recombinant protein generated by DNA technologies. Nucleotide sequences encoding Vitamin D Receptor from various animal species are available and characterized. Thus, the whole Vitamin D Receptor protein or the Ligand Binding Domain thereof used in the present invention as the receptor protein is, for example but without limitation, of mammalian origin (e.g a human, mouse or rat protein), or of avian origin, or of amphibian origin; alternatively, it is a mutated variant of any of such proteins.

Optionally, the whole Vitamin D Receptor protein or the Ligand Binding Domain thereof used as the receptor protein in the present invention further comprises or is coupled to an affinity tag, in order to substantially improve purification and/or detection procedures. Among the most common affinity tags, polyhistidine tags ("His-tag") attached at the C-terminal or N-terminal of the protein of interest are routinely employed in protein sciences and their use within the context of the present invention is therefore well within the knowledge of the person skilled in the art. Expressed His-tagged proteins are easily purified e.g. on matrices containing transitional metal ions, and the use of anti-His-tag antibodies represents a useful and known tool in localization and immunoprecipitation studies.

Therefore, in a preferred embodiment of the present invention, the whole Vitamin D Receptor protein or the Ligand Binding Domain thereof used as the receptor protein is a recombinant His-tagged fusion protein. However, other affinity tags such as, for example, Arg5, Strep-tag II, FLAG, fluorescein (FITC), Poly(A), Poly(dT) and biotin may be employed. Techniques for the production of epitope-tagged recombinant proteins are generally known in the art. In another preferred embodiment, the whole Vitamin D Receptor protein or the Ligand Binding Domain thereof used as the receptor protein is coupled to a chaperone protein or in general to any other protein which has a chaperone-like function, in order to help protein folding and/or improve stability. A receptor protein (i.e. the whole Vitamin D Receptor protein or the Ligand Binding Domain thereof, possibly coupled to an affinity tag or a chaperone or chaperone-like protein) bearing an amino acid sequence mutation aimed at improving stability may also be employed within the context of the invention.

As mentioned above, the detection method of the present invention involves the use of a capture moiety capable of binding the VDR-LBD/1,25(OH)$_2$D complex by specifically recognizing the conformationally modified VDR-LBD bound to 1,25(OH)$_2$D or analog thereof, without cross-reacting with uncomplexed VDR-LBD.

In a preferred embodiment, the capture moiety is an antibody as defined in appended claim 1.

Since an antibody having the binding specificity defined in appended claim 1 has been made available for the first time by the present inventors, the antibody per se also falls within the scope of the present invention.

Therefore, another aspect of the invention is an antibody which specifically binds the Ligand Binding Domain of Vitamin D Receptor of a complex formed between VDR-LBD and 1,25-dihydroxyvitamin D or an analog of 1,25-dihydroxyvitamin D without cross-reacting with uncomplexed VDR-LBD.

Preferably, the antibody of the invention is a monoclonal antibody. As described in the examples, a number of hybridoma clones producing monoclonal antibodies which are able to specifically recognize and bind to the conformationally modified VDR-LBD bound to 1,25(OH)$_2$D without substantially cross-reacting with uncomplexed VDR-LBD, were produced by the present inventors. One of such hybridoma clones, designated as 11B4H11H10, produces a monoclonal antibody which was fully characterized by sequencing, in order to identify the nucleic acid and amino acid sequences of its heavy and light chain variable domains. The CDRs (CDR1, CDR2 and CDR3) of both the heavy and light chain variable domains were also identified.

Such nucleic and amino acid sequences are illustrated in the Sequence Listing, which forms an integral part of the description; in the Sequence Listing, the amino acid and nucleic acid sequences of the heavy chain variable domain of 11B4H11H10 are designated as SEQ ID NO:7 and SEQ ID NO:8, respectively; the amino acid and nucleic acid sequences of the light chain variable domain of 11B4H11H10 are designated as SEQ ID NO:9 and SEQ ID NO:10, respectively; the CDRs of the heavy chain variable domain of 11B4H11H10 are designated as SEQ ID NOs: 1, 2 and 3 and the CDRs of the light chain variable domain of 11B4H11H10 are designated as SEQ ID NOs: 4, 5 and 6.

Therefore, according to a preferred embodiment, the antibody of the invention is a monoclonal antibody comprising a heavy chain variable domain and a light chain variable domain, wherein the heavy chain variable domain comprises at least one CDR selected from the group consisting of SEQ ID NO: 1, 2 and 3 and/or the light chain variable domain comprises at least one CDR selected from the group consisting of SEQ ID NO: 4, 5 and 6.

In a more preferred embodiment, the heavy chain variable domain comprises the CDRs SEQ ID NO: 1, 2 and 3 and/or the light chain variable domain comprises the CDRs SEQ ID NO: 4, 5 and 6.

In a particular embodiment, the heavy chain variable domain comprises the amino acid sequence SEQ ID NO:7 or is encoded by a nucleic acid comprising the sequence SEQ ID NO:8 and/or the light chain variable domain comprises the amino acid sequence SEQ ID NO:9 or is encoded by a nucleic acid comprising the sequence SEQ ID NO:10.

The term "antibody" as used in the present description encompasses a whole antibody molecule (including polyclonal, monoclonal, chimeric, humanized, or human versions having full length heavy and light chains) as well as an antigen binding antibody fragment. An "antibody fragment" includes any immunoglobulin fragment having the same binding specificity as the corresponding whole antibody. Such fragments are produced according to standard methods; cf. for example Harlow and Lane, "Antibodies, A Laboratory Manual", CSH Press, Cold Spring Harbor, USA, 1988. Non-limiting examples of antibody fragments include F(ah), Fab', F(ab')$_2$, F(v), single chain antibodies (scFv), F(c), F(d).

The antibody of the present invention is preferably produced by animal immunization. Briefly, monoclonal antibodies are generated by injecting animals, for example rats, hamsters, rabbits or mice, with an immunogen comprising the conformationally modified VDR-LBD bound to 1,25-(OH)$_2$ vitamin D or analog thereof, according to methods known per se (Costagliola et al., J Immunol 1998; 160:1458-65). The presence of specific antibody production is monitored after the initial injection and/or after a booster injection by performing an immunodetection assay on a serum sample obtained from the injected animals. From the animals which are found to produce the specific antibody(ies) of interest, spleen cells are removed and subsequently fused with a myeloma cell fusion partner to generate hybridoma cell lines which are then screened for their ability to secrete the antibody(ies) of interest, i.e. antibodies which specifically bind to the VDR-LBD of the complex formed between VDR-LBD and 1,25(OH)$_2$D or analog thereof.

In the detection method of the present invention, the detection of the captured VDR-LBD/1,25(OH)$_2$D complex may be accomplished through a wide range of techniques. For example, a detectable signal may be generated directly by employing a labeled receptor protein or indirectly via a labeled detector molecule which is capable of binding the VDR-LBD/1,25(OH)$_2$D complex captured by the capture moiety. Typically, the detector molecule is another antibody directed to an epitope on the VDR-LBD/1,25(OH)$_2$D complex which is different from the epitope recognized by the capture moiety of the invention (i.e., an anti-VDR-LBD detector antibody).

The detectable label may be any substance capable of producing a signal that is detectable by visual or instrumental means. Suitable labels for use in the present invention include for example fluorescent compounds, chemiluminescent compounds, radioactive compounds, enzymes and enzyme substrates, molecules suitable for colorimetric detection, binding proteins, epitopes, enzymes or substrates. In practice, any signal molecule or label known in the art may be incorporated in embodiments of the method and kit of We present invention.

Any assay format which enables contact between the biological fluid sample and the receptor protein comprising the Ligand Binding Domain of Vitamin D Receptor (VDR-LBD) is suitable for carrying out the detection method of the invention.

According to a preferred embodiment, the detection method of the invention is an in vitro immunoassay performed on a biological fluid sample of a subject or patient. Immunoassays include both homogeneous and heterogeneous assays, as well as competitive and non-competitive sandwich assays.

Figure 2:
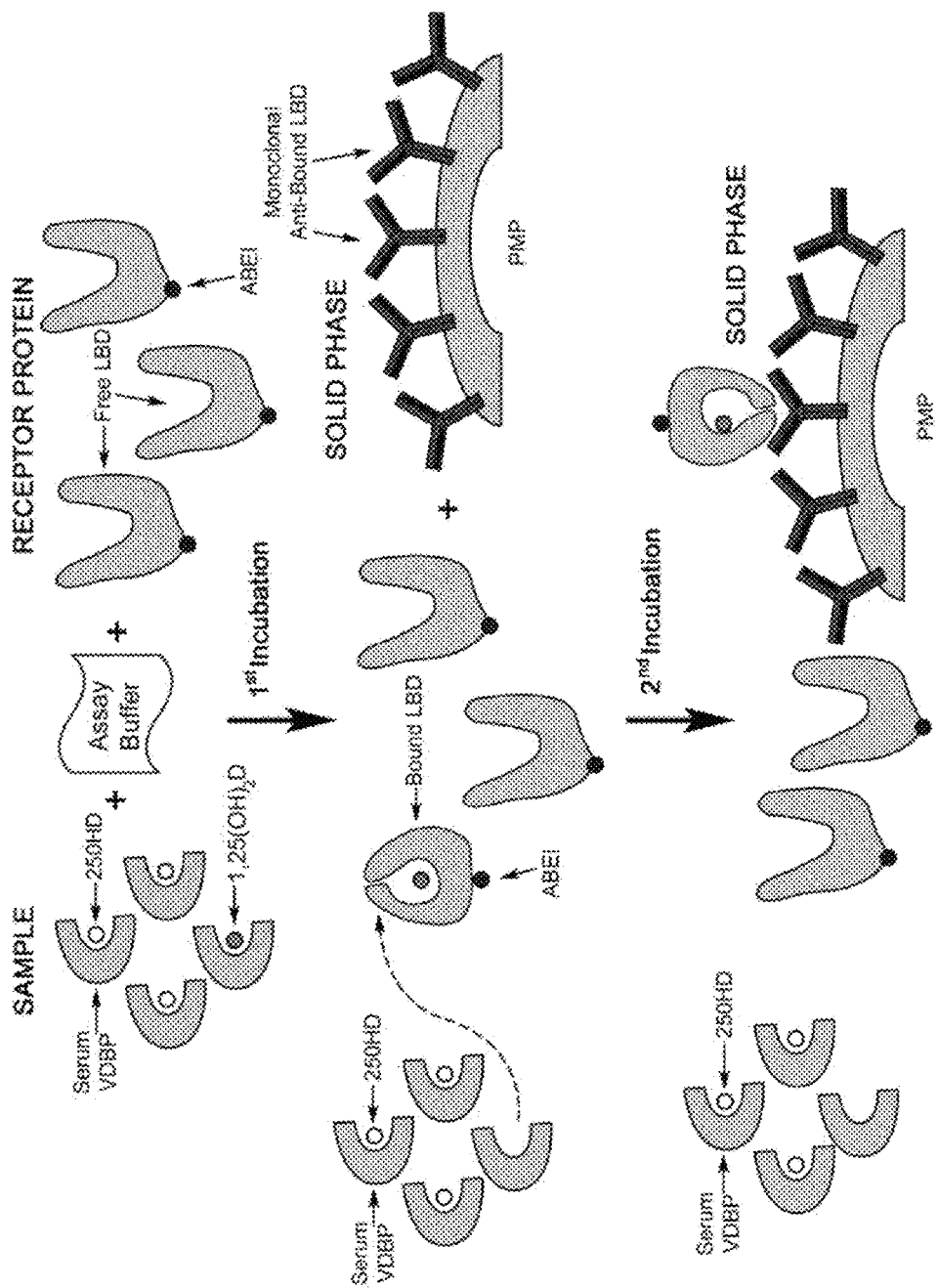

FIGS. 1 and 2 illustrate, by way of example, one-site, non-competitive immunoassays according to the invention, wherein the complex formed via the binding of 1,25(OH)$_2$D to the labeled receptor protein which comprises the Ligand Binding Domain of Vitamin D Receptor (VDR-LBD) is captured by the conformation-specific capture antibody of the invention (which in FIGS. 1 and 2 is designated as "Monoclonal Anti-Bound LBD") immobilized on a solid support. In the examples of FIGS. 1 and 2 the solid support is a paramagnetic particle (PMP) and the label is Amino-Butyl-Ethyl-Isoluminol (ABEI).

In the specific embodiment of FIG. 1, the step of adjusting the pH of the biological fluid sample with the assay buffer and the step of adding the receptor protein comprising the VDR-LBD to the sample, are performed simultaneously. In the specific embodiment of FIG. 2, such steps are carried out sequentially.

Figure 3:
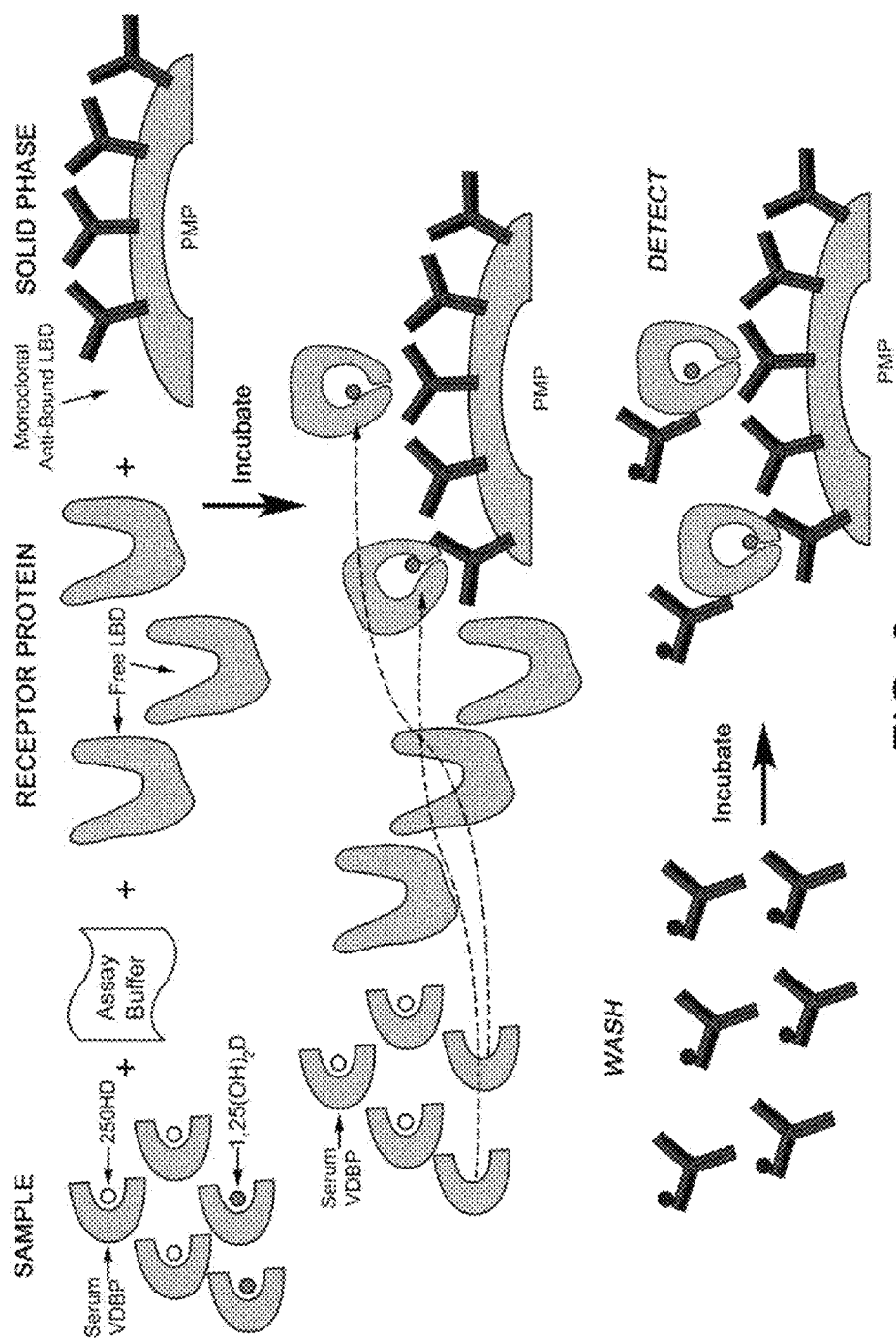
FIG. 3 illustrates a sandwich immunoassay.

FIG. 3 illustrates, by way of example, a sandwich immunoassay. The general features and procedures of sandwich immunoassays are well-established and known to the person skilled in the art. A sandwich immunoassay is a particularly preferred embodiment of the method of the present invention.

The sandwich immunoassay of FIG. 3 involves the binding of the VDR-LBD/1,25(OH)$_2$D complex to the conformation-specific capture antibody (designated as "Monoclonal Anti-Bound LBD") immobilized on a solid support (e.g. a paramagnetic particle, PMP) and the use of a labeled detector antibody as the second part of the sandwich. The detector antibody is either directly labeled or it is recognized by a conjugate consisting of a labeled anti-immunoglobulin antibody (in the specific example of FIG. 3 the detector antibody is directly labeled with ABEI). The amount of labeled antibody directly or indirectly bound to the VDR-LBD/1,25(OH)$_2$D complex is then measured by suitable means.

The sandwich immunoassay may involve the use of a tagged receptor protein comprising VDR-LBD in combination with an anti-tag detector antibody. In this embodiment, the detection of the VDR-LBD/1,25(OH)$_2$D complex captured by the conformational-specific capture antibody is achieved by the specific binding of the detector antibody to the tag which is present on the complex. Preferably, the tag is a polyhistidine tag. In a more specific embodiment, the tag is a chaperone protein.

The immunoassays falling within the scope of the invention may be in any suitable format, such as, for example, radioimmunoassays (RIA), chemiluminescence- or fluorescence-immunoassays, Enzyme-linked immunoassays (ELISA), Luminex-based bead arrays, protein microarray assays, or rapid test formats such as, for instance, immunochromatographic strip tests.

Depending on the format of the immunoassay, the capture antibody and/or the detector antibody may be immobilized on a solid support. Non limiting examples of suitable solid supports are the wells of a microtitre plate, the surface of a microparticle such as a latex, polystyrene, silica, chelating sepharose or magnetic heads, membranes, strips or chips.

As mentioned above, a further aspect of the present invention is a kit for detecting 1,25(OH)$_2$D or analog thereof in a biological fluid sample, the kit comprising the receptor protein and the capture moiety as defined above in connection with the method, as well as a binding buffer which has a pH comprised between 6 and 9. Preferred pH values are comprised between 7 and 8.6, such as 7.2, 7.3, 7.4, 7.5, 7.6, 7.7, 7.8, 7.9, 8.0, 8.1, 8.2, 8.3, 8.4, 8.5 or 8.6. Preferred but not limiting examples of the binding buffer for adjusting the pH of the test sample include 50 mM Tris buffer (pH 7.4), Hepes (6.5-7.5), PBS.

The kit of the invention may further comprise a solid support such as, without limitation, beads, microparticles, nanoparticles, super paramagnetic particles, a microtitre plate, a cuvette, a lateral flow device, a flow cell, or any surface to which a protein or peptide can be passively or covalently bound. Either the receptor protein or the capture moiety of the kit of the invention may be immobilized on the solid support.

Further, the kit of the invention may contain detection means as described above in connection with the detection method.

The following experimental section is provided purely by way of illustration and is not intended to limit the scope of the invention as defined in the appended claims.

EXAMPLES

Example 1: Expression and Purification of Rat VDR-LBD Protein

In order to produce recombinant VDR-LBD proteins to be used as suitable reagents for the methods and kits of the invention, a plasmid-based expression vector was constructed. Briefly, DNA coding for the ligand binding domain of the vitamin D receptor from *Rattus norvegicus* residues 116-423 with deletion of a 47 amino acid internal loop (165-211) (rVDR-LBD) was cloned into the pET-29b plasmid (Novagen) by using the Nde I/Bgl II restriction site combination. To facilitate the detection and purification of recombinant VDR-LBD protein, a polyhistidine tag can be added at the C-terminus of the protein of interest by cloning a His tag coding sequence downstream of the VDR-LBD coding sequence, followed by a stop codon.

The plasmids encoding the VDR-LBD protein were expressed as inclusion bodies in BL21-CodonPlus(DE3)-RIPL (Stratagene) cells grown in LB supplemented with kanamycin (40 μg/L) and chloramphenicol (40 μg/L). A starter culture (5 mL) was inoculated with a single bacterial colony and grew in a 14 mL tube at 37° C. (250 rpm) for 6 hrs to reach optical density (OD600) of ~1. The starter culture was diluted into an overnight culture (35 mL) by 2500-fold and grew in a 125 mL flask at 30° C. (250 rpm) for 15 h (typical OD600~3.7). The overnight culture was diluted in 0.5 L of the expression media in a 2 L flask with OD600 of ~0.09. The culture grew for ~2.5 h (250 rpm) to OD600 of 0.6-0.8 and the expression of VDR-LBD was induced by the addition of IPTG to a final concentration of 0.35 mM. The culture continued growing at 37° C. for 6 h before the cells were harvested by centrifugation at 5000 rpm (GS3 rotor) at 4° C. for 15 min. The freshly collected cell pellet (typically 5.5 g/L of culture) was stored at −80° C. for further protein purification.

The cell pellet (5.5 g) was resuspended in 135 mL of lysis buffer containing 50 mM Tris-HCl (pH 8.0), 2 mM EDTA, 10 mM DTT, 0.3 mM phenylmethylsulfonyl fluoride, and 0.5 mg/mL lysozyme, and subjected to sonication with a sonic dismembrator (Fisher). The pellet, including cell debris and inclusion bodies, was obtained by centrifugation at 11000 rpm (SS34 rotor) at 4° C. for 15 mM, and washed with 200 mL of the wash buffer (50 mM Tris-HCl, 2 mM EDTA, 100 mM NaCl, pH 8.0) followed by 200 mL of the same wash buffer with 0.5% (v/v) Triton X-100. After each addition, the slurry was stirred gently for 5 min and then centrifuged at 12000 rpm at 4° C. for 20 min. The final pellet was suspended very gently in 200 mL of denaturing buffer containing 40 mM Tris-acetic acid (pH 7.6), 2 mM EDTA, 6 M guanidine-HCl and 100 mM DTT, and stirred for 2 h at room temperature. A clear solution was obtained by centrifugation at 12000 rpm at 4° C. for 20 min. The supernatant was dialyzed against 20 L of dialysis buffer containing 25 mM $NaH_2PO_4$—$Na_2HPO_4$ (pH 7.4), 50 mM KCl, and 2 mM DTT at 4° C. overnight. The next day, white precipitate was removed by centrifugation and the supernatant was recovered and dialysis was continued for another 24 h with two changes of the buffer containing 16 mM HEPES (pH 7.4), 25 mM NaCl, 15 mM KCl, and 2 mM DTT. The protein solution was concentrated in an Amicon centrifugal filter (10K MWCO) and exchanged into the final buffer containing 16 mM HEPES (pH 7.4), 25 mM NaCl, 15 mM KCl, and 10 mM TCEP. Buffer exchange was done by repeated dilution and concentration to remove DTT that is incompatible with the His-tag beads. The purity of the protein was analyzed by 12% SDS-PAGE. Protein concentration was determined by the Bradford method using BSA as standard (coefficient 0.055 $\mu g^{-1}$ $cm^{-1}$). Typical yield of VDR-LBD is 25-30 mg/L of culture and highly dependent upon the expression level, which is determined by the healthiness of the culture, and the dialysis procedure.

Example 2: Generation of Conformation-Specific Monoclonal Antibodies Capable of Recognizing the VDR-LBD/1,25(OH)$_2$D Complex The strategy pursued by the present inventors for the generation of conformation-specific antibodies was based on the exploitation of the complex consisting of the binding domain of Vitamin D Receptor (VDR-LBD) bound to 1,25 (OH)$_2$D as the immunogen. Individual use aliquots of the immunogen formulated with the appropriate adjuvant were injected into BALB/c mice. Following 4-, 6- and 8-weeks, lymphocytes from mice spleens were fused with SP2/0 mouse myeloma cells using polyethylene glycol (PEG) as fusion agent. The hybrid cells were plated over 384 wells in a high through-put 96 well culture plate format.

Antigen-specific immune activity was determined by ELISA directly onto the master fusion plates, using the immunogen of interest, i.e. the VDR-LBD/1,25(OH)$_2$D complex, and the unbound vitamin D ligand binding domain alone as negative control. Briefly, 96-well microtiter plates were coated with 100 nl of 0.56 ng/ml His-tagged recombinant VDR-LBD protein in the unbound form or pre-bound with 1,25(OH)$_2$D, respectively. The pre-binding reaction was carried-out by incubating the VDR-LBD protein overnight in the presence of three molar excess of 1,25(OH)$_2$D (1 mg/ml). Protein adsorption onto the microtiter plates was achieved via specific interactions between the polyhistidine tag and a coating of nickel ions present on the wells surface.

After protein adsorption, the plates were washed with PBS-T (0.1% Tween 20 in PBS) and incubated with 100 nl of the monoclonal antibodies under examination diluted 1:16000, for 1 hour at room temperature, with gentle mixing. Following incubation, the plates were washed three times with PBS-T and incubated with 100 nl of HRP-conjugated goat anti-mouse IgGs (1 mg/ml) diluted 1:30000 in PBS-T, for 1 hour at room temperature. The washed plates were then incubated with 100 µl/well of TMB substrate at room temperature for 10 minutes. The reaction was stopped by adding 150 µl/well of 1% HCl solution. The absorbance at 450 nm was measured using a microplate reader.

Such screening strategy enabled the detection and selection of antibody-secreting clones showing specificity towards the VDR-LBD/1,25(OH)$_2$D complex only and not for the unbound ligand binding domain (Table 1). Then, the selected hybridomas were cloned by the limiting dilution method and re-screened according to the above-described ELISA method. Clones with the desired titer and specificity were sub-cloned in order to stabilize the antibody expression.

Each of the selected clones was initially tested to determine the isotype of the mouse immunoglobulin and subsequently expanded to production scale. Following the clone expansion, mouse IgGs were isolated by protein A affinity purification using the AKTAprime plus and subjected to a buffer exchange using a Hitrap desalting column to 1×DPBS buffer. The antibody sample thus obtained was sterilized using a 0.2 nm filter, the sample concentration was estimated and the product was sterile-packaged in a polypropylene tube and stored at 4° C.

As a result of the above-described studies, the hybridoma clone named 11B4H11H10 was selected for further analysis.

TABLE 1

(ELISA screening data obtained with 4 antibodies according to the invention which specifically bind the anti-VDR-LBD/ 1,25(OH)$_2$D complex)

| Antibody Clone ID | ELISA absorbance at 450 nm | | |
|---|---|---|---|
| | VDR-LBD/1,25(OH)$_2$D complex | unbound VDR-LBD | Ratio |
| 10A3 | 3.659 | 0.103 | 35.5 |
| 11B4 | 3.028 | 0.121 | 25.0 |
| 12C11 | 0.569 | 0.090 | 6.32 |
| 8E2 | 0.480 | 0.382 | 1.26 |

The above-illustrated selection method may also be used to identify further hybridoma clones secreting antibodies according to the present invention, i.e. mAbs or functional fragments thereof which are capable of specifically binding the Ligand Binding Domain of Vitamin D Receptor bound to 1,25-dihydroxy-vitamin D or analog thereof.

Example 3: Identification of the DNA Consensus Sequence of the Immunoglobulin G VH and VL Gene, Expressed by Hybridoma Clone 11B4H11H10

A master stock vial of 11B4H11H10 was thawed and expanded to generate a representative number of cells for cDNA library constructions. Briefly, 1×10$^7$ hybridoma cells were isolated from an actively log growth culture of cells in a 75 cm$^2$ flask and centrifuged at 500×g for 4 minutes in a polypropylene 50 cm$^2$ sterile centrifuge tube. The total RNA was isolated using TRIzol® Reagent, Invitrogen, and quantified on a Nanodrop™ Hybridoma total RNA (500 ng) was reverse-transcribed using the oligo dT primer procedure. Mouse immunoglobulin variable heavy (Vh) and variable light chains (Vl) were amplified from the cDNA library (RT-PCR) by using specific primers. Those amplified chains were independently inserted, in a random orientation, into a TOPO vector (Invitrogen) by TA cloning. The ligation product was transformed by electroporation into an electrocompetent maintenance strain of E. coli.

Twenty independent bacterial colonies were selected from each transformation plate and expanded by inoculation into 10 ml of LBA broth (100 ng/ml ampicillin) in a 15 ml polypropylene snap cap tube and growth at 37° C. overnight with 250 rpm orbital shaking. Thus, twenty purified plasmid DNA were generated for both Vh and Vl.

Each of the initial twenty Vh and Vl TOPO plasmids was screened by automated DNA sequencing (Functional Biosciences, Madison, Wis.) with a single replicate forward (5'-3') reaction using T7 sequencing primer to determine whether a full length Vh or Vl insert was present. Upon sequence alignment, a single representative Vh and Vl emerged thus indicating that the hybridoma population at the time of RNA isolation was monoclonal.

Up to ten representative plasmids for both Vh and Vl, which contain the corresponding full-length insert, were selected for additional replicates of DNA sequencing. More specifically, each plasmid underwent two additional T7 forward and BGH reverse reactions to build the consensus sequence.

DNA alignments were performed using CLC Workbench in order to generate the novel mouse immunoglobulin variable heavy and variable light consensus sequence. Upon translation of the identified DNA consensus sequences into amino acid stretches, NCBI BLAST was employed for Vh and Vl protein domain analysis to confirm that the sequences are mouse immunoglobulin genes and to map important structural domains, including the Complementarity determining regions (CDRs).

The DNA consensus sequences of the monoclonal antibody designated as 11B4H11H10, as well as the CDRs thereof, are illustrated in the Sequence Listing.

Example 4: 1,25(OH)$_2$D Assay

One of the preferred embodiment of the assay of the invention was developed as follows. Paramagnetic microparticles (PMPs) (Dynal, Norway) were coated with the 11B4 monoclonal antibody following the supplier instructions. The recombinant VDR-LBD that was used in the assay was prepared as described in Example 1, and was coupled to an affinity tag (designated in the following as "TAG"). The 11B4H11H10 monoclonal antibody that was used in the assay was prepared as described in Example 2. A mouse monoclonal anti TAG antibody was conjugated with cyclic AminoButhylEthylisoluminol (cABEI) in PBS buffer pH 7.4. The calculated cABEI incorporation was from 2-3 molecules per antibody molecule. Calibrators were prepared by adding different concentrations of an ethanolic solution of 1,25(OH)$_2$D into a steroid-free, charcoal-stripped human serum. The assay buffer formulation consisted of TRIS 50 mM pH 7.4, CHAPS 0.02%, EDTA 1 mM, heparin at 8 mg/ml and 1% mouse serum to mitigate heterophilic human anti mouse (HAMA) interferences.

A major challenge of an automated assay not using any off-line pre-analytical/sample pre-treatment steps is the ability of the assay to specifically capture and detect the whole amount of 1,25(OH)$_2$D, or analogues of the active form of vitamin D, in a biological matrix (e.g. serum or plasma) without interference by other vitamin D metabolites such as 25(OH)D, 24,25(OH)$_2$D and 25,26(OH)$_2$D which can be present at levels 1000-fold higher than 1,25(OH)$_2$D. This challenge is further complicated by the presence of Vitamin D binding protein (DBP) and albumin, which are abundant in circulation and serve as the major binding proteins for 25(OH)D, 1,25(OH)$_2$D, and other metabolites of vitamin D, whereby 85% to 90% is bound to DBP and 10 to 15% is bound to albumin. Furthermore, DBP levels increases up to 2-5 fold in high-estrogen states, such as pregnancy.

Therefore, in order to verify the capability of the assay of the invention to specifically capture and detect the whole amount of circulating 1,25(OH)$_2$D in a VDBP-independent manner, the inventors prepared a panel of human serum samples (N=17; 8 apparently healthy individuals and 9 pregnant women) spanning the measuring range of the assay. The expected 1,25(OH)$_2$D values (pg/mL) in these 17 samples were determined by using a FDA-approved 1,25 (OH)$_2$D radioimmunoassay from DiaSorin Inc. in Stillwater, Minn. USA (Part No. 65100E/100 Tubes; 1,25-Dihydroxyvitamin D), which was then used as a reference method.

The assay schematically illustrated in FIG. 3 was carried out on the DiaSorin LIAISON® analyzer (Saluggia, Italy). First, 50 μl of human serum sample was incubated with 100 μl of assay buffer and 50 μl of VDR-LBD-TAG for 30 minutes. Next, 20 μl of PMPs coated with 11B4H11H10 monoclonal antibody were added and the reaction mixture was incubated for an additional 30 minutes. After washing the reaction mixture, 40 μl of cABEI-conjugated anti TAG monoclonal antibody was added and the reaction mixture incubated for an additional 30 min. After a second wash, trigger solutions were added and the reaction mixture was read as Relative Lights Units (RLUs) in the analyzer reading chamber.

Figure 4:
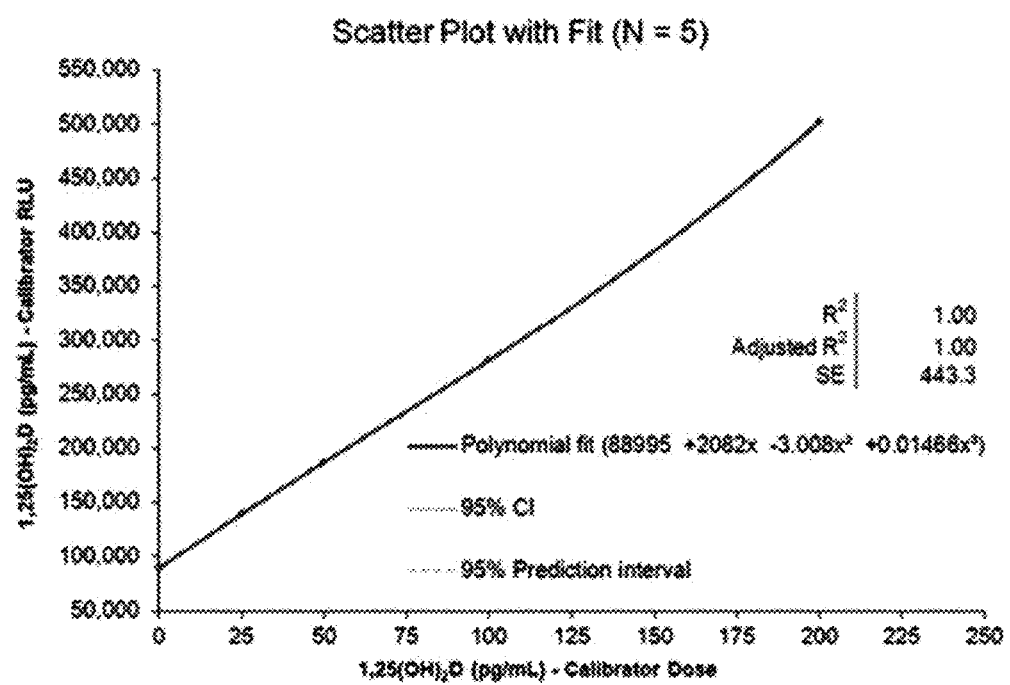
FIG. 4 illustrates a standard curve comparing the 1,25 $(OH)_2D$ assay with the DiaSorin RIA as the reference method; the RLUs obtained with each sample were transformed into pg/mL based on the RLUs vs. dose (pg/mL) obtained.
Figure 5A:
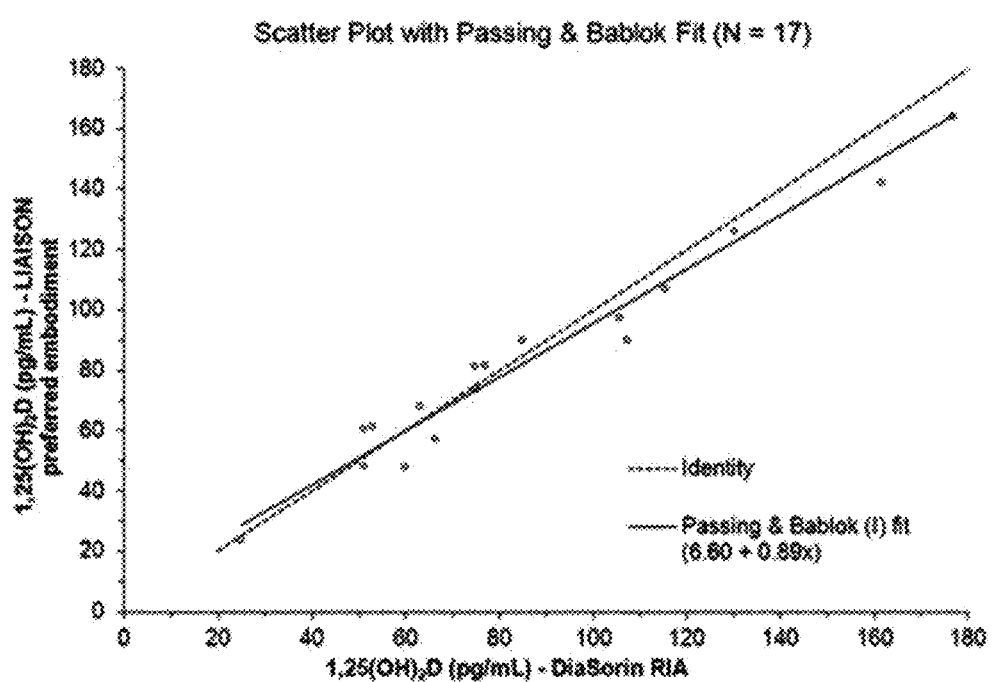
FIGS. 5a, 5b and 5c illustrate calibrator response (RLU) plotted against dose (pg/mL) using a Scatter Plot with third order polynomial fit; sample RLUs were transformed into pg/mL (Table 2) where the correlation between the assay and reference method was carried out by using Passing & Bablok fit (FIG. 5a), Linear Regression (FIG. 5b), and Bland Altman % Difference plot analyses (FIG. 5c).
Figure 5B:
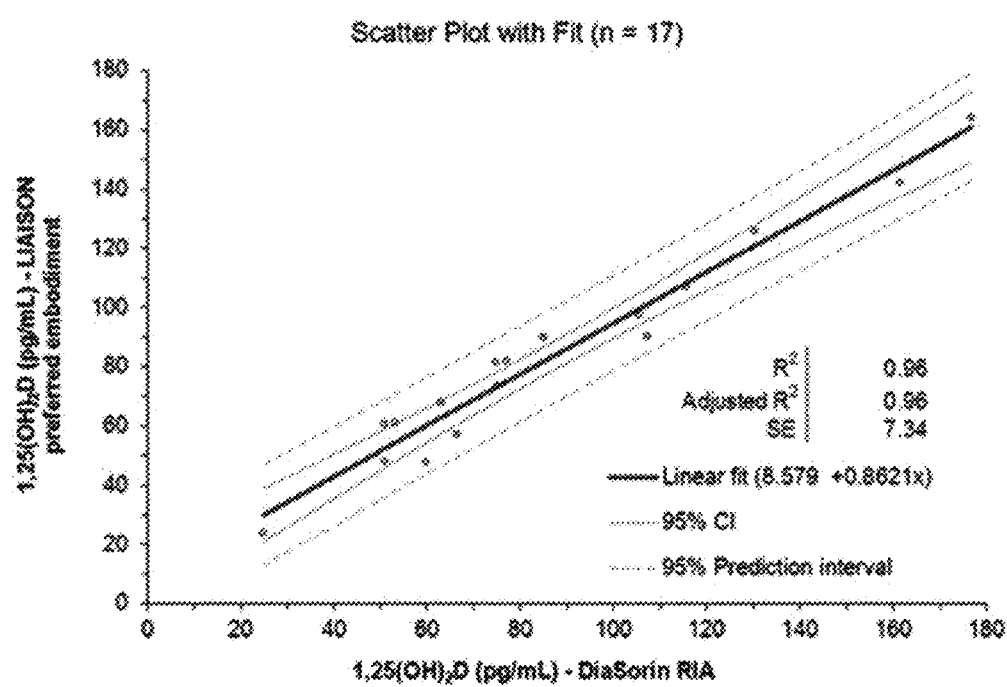
Figure 5C:
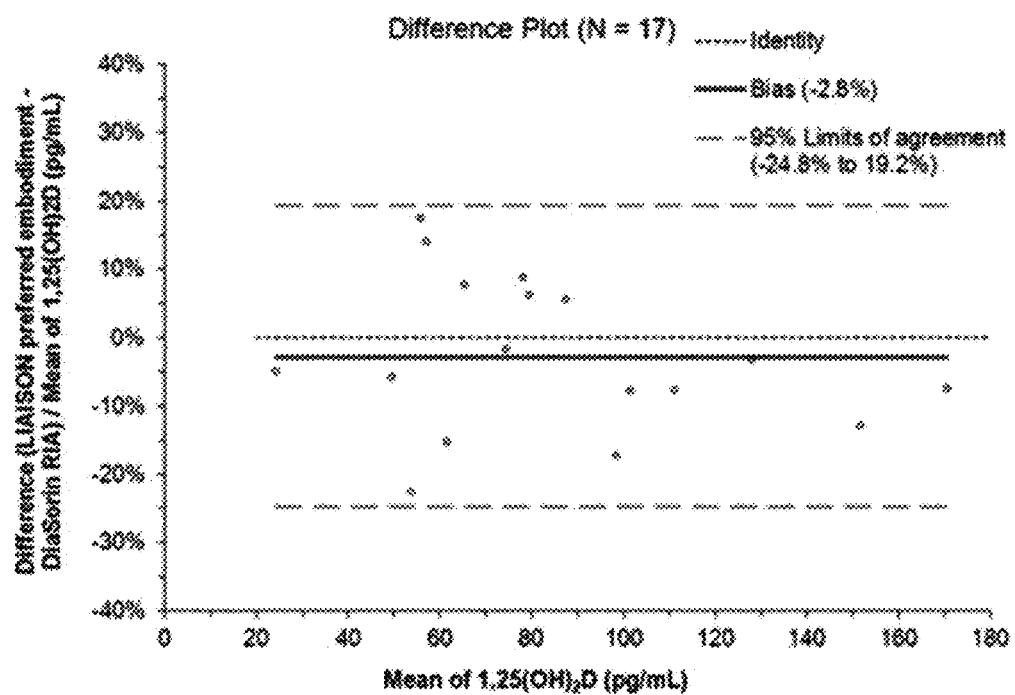

To compare the 1,25(OH)$_2$D assay of the invention with the DiaSorin RIA as the reference method, the RLUs obtained with each sample were transformed into pg/mL based on the RLUs vs. dose (pg/mL) obtained with the standard curve illustrated in FIG. 4. The standard curve of FIG. 4 was obtained as follows. Standard curve calibrators were prepared by adding different concentrations of an ethanolic solution of 1,25(OH)$_2$D into a steroid-free, charcoal-stripped human serum. Calibrator response (RLU) was plotted against dose (pg/mL) using a Scatter Plot with third order polynomial fit. Then, sample RLUs were transformed into pg/mL (Table 2) and the correlation between the assay and reference method was carried out by using Passing & Bablok fit, Linear Regression, and Bland Altman % Difference plot analyses The results obtained are shown in FIGS. 5A, 5B and 5C, respectively. The analyses demonstrate that the doses determined with the assay of the invention and the DiaSorin RIA reference assay are substantially equivalent (slope of 0.89, intercept of 6.6 pg/mL, $R^2$ of 0.96, and mean % Difference of −2.8%), thus indicating that the assay of the invention is capable of accurately capturing and detecting the whole amount of circulating 1,25(OH)$_2$D in human serum independently of DBP serum concentrations.

Figure 6:
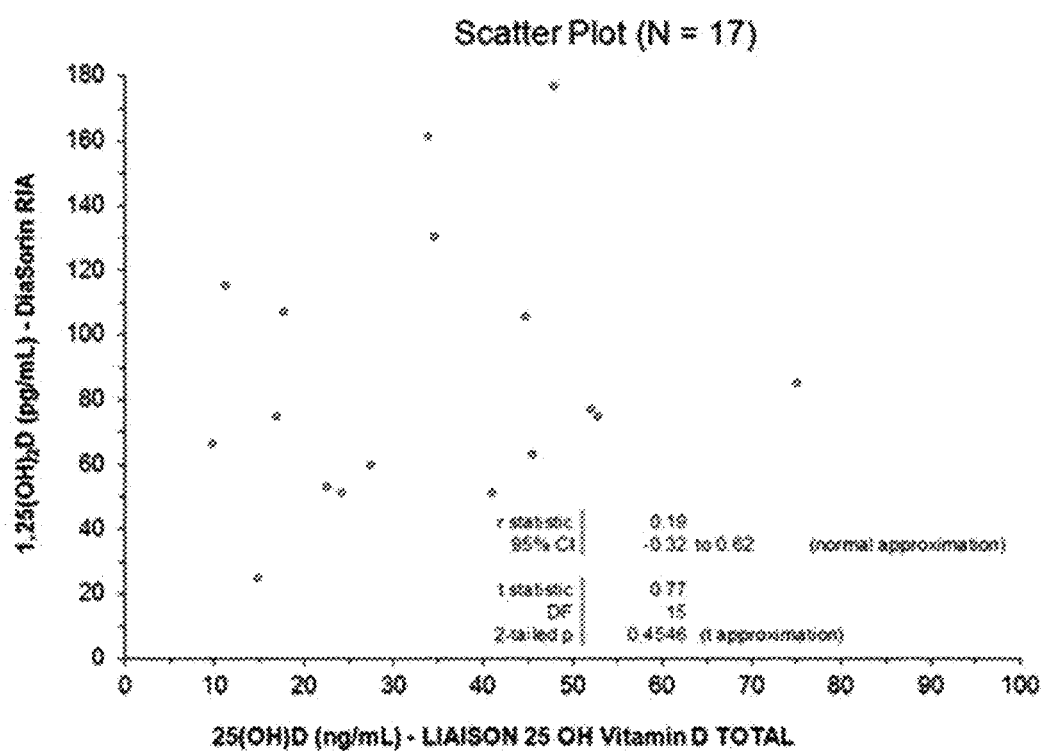
FIG. 6 illustrates the specific recovery of $1,25(OH)_2D$ in human serum, where the concentration (ng/mL) of total 25(OH)D in each panel sample (N=17) was determined using the FDA 510(k) cleared LIAISON® 25 OH Vitamin D TOTAL Assay (Part No. 310600, DiaSorin Inc., Stillwater, Minn., USA); since there was no correlation between the 510(k) cleared DiaSorin RIA $1,25(OH)_2D$ doses and the 510(k) cleared LIAISON® 25 OH Vitamin D TOTAL Assay 25(OH)D doses.

Finally, to demonstrate the specific recovery of 1,25(OH)$_2$D in human serum, the concentration (ng/mL) of total 25(OH)D in each panel sample (N=17) was determined using the FDA 510(k) cleared LIAISON® 25 OH Vitamin D TOTAL Assay (Part No. 310600, DiaSorin Inc., Stillwater, Minn., USA). Since there was no correlation between the 510(k) cleared DiaSorin RIA 1,25(OH)$_2$D doses and the 510(k) cleared LIAISON® 25 OH Vitamin D TOTAL Assay 25(OH)D doses (FIG. 6), we concluded that the 1,25(OH)$_2$D assay of the invention specifically and quantitatively recovers the whole amount of 1,25(OH)$_2$D in human serum independently of serum total 25(OH)D concentrations. These results are illustrated in FIG. 6, which shows that there was no significant correlation (p=0.4546) between 1,25(OH)$_2$D and 25(OH)D doses.

TABLE 2

(RLUs obtained with each sample were transformed into dose (pg/mL) based on the RLUs vs. dose obtained with the LIAISON standard curve in FIG. 4. Doses spanned the assay measuring range from 23.8 pg/mL (minimum) to 164.0 pg/mL (maximum), with a mean of 83.54 pg/mL and 95% CI 65.04 to 102.03 pg/mL).

| No. | Sample ID | Gender | Type | LIAISON 1,25(OH)$_2$D RLUs | Dose (pg/mL) |
|---|---|---|---|---|---|
| 1 | M10284 | Male | Apparently Healthy | 246,408 | 81.9 |
| 2 | M10279 | Male | Apparently Healthy | 231,717 | 73.7 |
| 3 | M10302 | Male | Apparently Healthy | 183,344 | 48.1 |
| 4 | F20378 | Female | Apparently Healthy | 182,691 | 47.8 |
| 5 | F20436 | Female | Apparently Healthy | 260,932 | 89.8 |
| 6 | F20198 | Female | Apparently Healthy | 208,126 | 60.7 |
| 7 | F20151 | Female | Apparently Healthy | 221,471 | 68.0 |
| 8 | F20416 | Female | Apparently Healthy | 137,640 | 23.8 |
| 9 | 8316745 | Female | Pregnant | 245,686 | 81.5 |
| 10 | 8316205 | Female | Pregnant | 419,906 | 164.0 |
| 11 | 8315465 | Female | Pregnant | 276,473 | 97.5 |
| 12 | 8315505 | Female | Pregnant | 201,329 | 57.1 |
| 13 | 8316605 | Female | Pregnant | 208,752 | 61.1 |
| 14 | 8316585 | Female | Pregnant | 373,007 | 142.0 |
| 15 | 8316765 | Female | Pregnant | 298,588 | 107.0 |
| 16 | 8316815 | Female | Pregnant | 261,589 | 90.1 |
| 17 | 8315375 | Female | Pregnant | 338,801 | 126.0 |

What is claimed is:

1. A method for detecting 1,25-dihydroxyvitamin D (1,25(OH)$_2$D) or an analog thereof selected from one or more of the group consisting of 19-nor-1α-25-dihydroxyvitamin D$_2$, 1α-hydroxyvitamin D$_2$, 1α-hydroxyergocalciferol and 2-methylene-19-nor-(20S)-1α,25-(OH)$_2$D$_3$, in a biological fluid sample, the method comprising the steps of:
   (i) adjusting the pH of the biological fluid sample to a value comprised between 6 and 9 and simultaneously or subsequently adding to the biological fluid sample a receptor protein comprising the Ligand Binding Domain of the *Rattus norvegicus* Vitamin D Receptor (VDR-LBD), under conditions sufficient for forming a complex of 1,25-dihydroxyvitamin D or said analog thereof bound to the VDR-LBD of the receptor protein;
   (ii) incubating said complex in the presence of a capture moiety, wherein said capture moiety is a monoclonal antibody or a fragment of the monoclonal antibody, wherein said monoclonal antibody and said monoclonal antibody fragment comprise:
   heavy chain CDR1, CDR2, and CDR3 domains that respectively are the amino acid sequences of SEQ ID NOs: 1, 2 and 3; and
   light chain CDRs that respectively are the amino acid sequences of SEQ ID NOs: 4, 5 and 6; and
   wherein said incubation is under conditions sufficient to permit said monoclonal antibody or said monoclonal antibody fragment to bind said complex and to form a captured complex; and
   (iii) detecting said captured complex.

2. The method according to claim 1, wherein the receptor protein is the whole Vitamin D Receptor protein or the Ligand Binding Domain (LBD) thereof in an isolated or engineered form.

3. The method according to claim 1, wherein the capture moiety is immobilized on a solid support.

4. The method according to claim 1, wherein the biological fluid sample is whole blood, plasma, serum or urine.

5. The method according claim 1, wherein in step (i) the pH of the biological fluid sample is adjusted to a value comprised between 7 and 8.6.

6. The method according to claim 1, which is a sandwich immunoassay.

7. The method according to claim 6, wherein in step (iii) said captured complex is detected using a labeled anti-VDR-LBD detector antibody.

* * * * *

SEQUENCE LISTING

```
<160> NUMBER OF SEQ ID NOS: 10

<210> SEQ ID NO 1
<211> LENGTH: 10
<212> TYPE: PRT
<213> ORGANISM: Mus musculus

<400> SEQUENCE: 1

Gly Phe Thr Phe Ser Asn Phe Gly Met Gln
1               5                   10

<210> SEQ ID NO 2
<211> LENGTH: 10
<212> TYPE: PRT
<213> ORGANISM: Mus musculus

<400> SEQUENCE: 2

Tyr Ile Ser Ser Gly Ser Ser Thr Ile Tyr
1               5                   10

<210> SEQ ID NO 3
<211> LENGTH: 9
<212> TYPE: PRT
<213> ORGANISM: Mus musculus

<400> SEQUENCE: 3

Ser Gly Leu Ile Asp Gly Phe Ala Tyr
1               5

<210> SEQ ID NO 4
<211> LENGTH: 11
<212> TYPE: PRT
<213> ORGANISM: Mus musculus

<400> SEQUENCE: 4

His Ala Ser Gln Gly Ile Ser Ser Asn Ile Gly
1               5                   10

<210> SEQ ID NO 5
```

```
<211> LENGTH: 7
<212> TYPE: PRT
<213> ORGANISM: Mus musculus

<400> SEQUENCE: 5

His Gly Thr Asn Leu Glu Asp
1               5

<210> SEQ ID NO 6
<211> LENGTH: 9
<212> TYPE: PRT
<213> ORGANISM: Mus musculus

<400> SEQUENCE: 6

Val Gln Tyr Ala Gln Phe Pro Phe Thr
1               5

<210> SEQ ID NO 7
<211> LENGTH: 110
<212> TYPE: PRT
<213> ORGANISM: Mus musculus

<400> SEQUENCE: 7

Gly Gly Leu Val Gln Pro Gly Gly Ser Arg Lys Leu Ser Cys Ala Ala
1               5                   10                  15

Ser Gly Phe Thr Phe Ser Asn Phe Gly Met Gln Trp Val Arg Gln Ala
            20                  25                  30

Pro Glu Lys Gly Leu Glu Trp Val Ala Tyr Ile Ser Ser Gly Ser Ser
        35                  40                  45

Thr Ile Tyr Tyr Ala Asp Thr Val Lys Gly Arg Phe Thr Ile Ser Arg
    50                  55                  60

Asp Asn Pro Lys Asn Thr Leu Phe Leu Gln Met Thr Ser Leu Arg Ser
65                  70                  75                  80

Glu Asp Thr Ala Met Tyr Tyr Cys Ala Arg Ser Gly Leu Ile Asp Gly
                85                  90                  95

Phe Ala Tyr Trp Gly Gln Gly Thr Thr Val Thr Val Ser Ser
            100                 105                 110

<210> SEQ ID NO 8
<211> LENGTH: 330
<212> TYPE: DNA
<213> ORGANISM: Mus musculus

<400> SEQUENCE: 8
ggaggcttag tgcagcctgg agggtcccgg aaactctcct gtgcagcctc tggattcact      60
ttcagtaact ttggaatgca gtgggttcgt caggctccag agaagggct agagtgggtc      120 gcatacatca gtagtggcag tagtaccatc tactatgcag acacagtgaa gggccgattc      180
accatatcca gagacaatcc caagaatacc ctgttcctgc aaatgaccag tctaaggtct      240
gaggacacgg ccatgtatta ctgtgcaaga tcgggtttaa tcgacgggtt tgcttactgg      300
ggccaaggga ccacggtcac cgtctcctca                                       330

<210> SEQ ID NO 9
<211> LENGTH: 95
<212> TYPE: PRT
<213> ORGANISM: Mus musculus

<400> SEQUENCE: 9

Gln Ser Pro Ser Ser Met Ser Val Ser Leu Gly Asp Thr Val Ser Ile
1               5                   10                  15
```

```
Thr Cys His Ala Ser Gln Gly Ile Ser Ser Asn Ile Gly Trp Leu Gln
            20                  25                  30

Gln Lys Pro Gly Lys Ser Phe Lys Gly Leu Ile Tyr His Gly Thr Asn
            35                  40                  45

Leu Glu Asp Gly Val Pro Ser Arg Phe Ser Gly Ser Gly Ser Gly Ala
 50                  55                  60

Asp Tyr Ser Leu Thr Ile Ser Ser Leu Glu Ser Glu Asp Phe Ala Asp
 65                  70                  75                  80

Tyr Tyr Cys Val Gln Tyr Ala Gln Phe Pro Phe Thr Phe Gly Ser
                 85                  90                  95

<210> SEQ ID NO 10
<211> LENGTH: 287
<212> TYPE: DNA
<213> ORGANISM: Mus musculus

<400> SEQUENCE: 10
cagtctccat cctccatgtc tgtatctctg ggagacacag tcagcatcac ttgccatgca      60
agtcagggca ttagcagtaa tatagggtgg ttgcagcaga aaccagggaa atcatttaag     120
ggcctgatct atcatggaac caacttggaa gatggagttc catcaaggtt cagtggcagt     180
ggatctggag cagattattc tctcaccatc agcagcctgg aatctgaaga ttttgcagac     240
tattactgtg tacagtatgc tcagtttcca ttcacgttcg gctcggg                   287
```